United States Patent [19]
Koenig et al.

[11] 3,939,184
[45] Feb. 17, 1976

[54] PRODUCTION OF CARBONYL COMPOUNDS SUBSTITUTED IN α-POSITION

[75] Inventors: Horst Koenig; Horst Metzger; Werner Reif, all of Ludwigshafen (Rhine), Germany

[73] Assignee: Badische Anilin- & Soda-Fabrik Aktiengesellschaft, Ludwigshafen (Rhine), Germany

[22] Filed: Mar. 26, 1973

[21] Appl. No.: 344,632

Related U.S. Application Data

[60] Division of Ser. No. 863,770, Oct. 2, 1969, Pat. No. 3,821,277, which is a continuation of Ser. No. 505,229, Oct. 26, 1965, abandoned.

[30] Foreign Application Priority Data

| Oct. 30, 1964 | Germany | 1226562 |
|---|---|---|
| Oct. 30, 1964 | Germany | 1226563 |
| Oct. 30, 1964 | Germany | 1238454 |

[52] U.S. Cl. ......... 260/349; 260/562 B; 260/153 A; 260/562 K; 260/453 AL; 260/562 S; 260/586 R; 260/453 AR; 260/590 R; 260/454; 260/593 H; 260/593 R; 260/455 R; 260/594; 260/464; 260/465 D; 260/465 F; 260/465 G; 260/465 H; 260/465.4; 260/465.6; 260/465.7; 260/465.8 R; 260/470; 260/471 A; 260/473 A; 260/475 SC; 260/481 R; 260/482 R; 260/483; 260/484 R; 260/485 H; 260/485 J; 260/485 R; 260/557 R; 260/561 B; 260/561 HL; 260/561 K; 260/561 R; 260/561 S

[51] Int. Cl.² .............. C07C 69/66; C07C 117/00; C07C 121/76; C07C 122/00

[58] Field of Search ............ 260/465 F, 349, 465 D, 260/453 AL, 454, 455 R, 465.8 R, 590, 593 R, 481 R, 483, 484 R

[56] References Cited
OTHER PUBLICATIONS
Hoffmann; J. Org. Chem., pp. 823–824 (1965).

*Primary Examiner*—Lewis Gotts
*Assistant Examiner*—Dolph H. Torrence
*Attorney, Agent, or Firm*—Johnston, Keil, Thompson & Shurtleff

[57] ABSTRACT

Production of carbonyl compounds substituted in the α-position and having the formula:

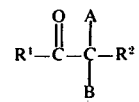

wherein $R^1$ is alkyl, aralkyl, phenyl, toluyl, naphthyl, alkoxy or amino; $R^2$ is hydrogen

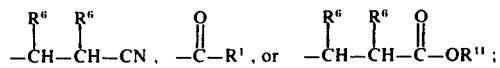

A is hydrogen, alkyl, halo or

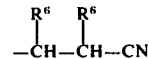

$R^6$ is hydrogen or methyl, and $R^{11}$ is alkyl; wherein said compounds are formed by reacting a sulfur ylide having the formula:

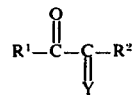

wherein Y is the radical

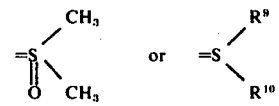

and $R^9$ and $R^{10}$ are alkyl or phenyl, with a solution containing both an electrophilic agent A' that is converted into the radical A and a nucleophilic agent B' that is converted into the radical B. The resulting carbonyl compounds are useful as starting materials for the production of paper, textile, and leather auxiliaries, plant protection agents, alkyd resins, polyesters and polyamides.

1 Claim, No Drawings

PRODUCTION OF CARBONYL COMPOUNDS SUBSTITUTED IN α-POSITION

This is a division of application Ser. No. 863,770, filed Oct. 2, 1969, Pat. No. 3,821,277, which is a continuation of application Ser. No. 505,229, filed Oct. 26, 1965, abandoned.

This invention relates to a process for the production of carbonyl compounds substituted in α-position, in which sulfur ylides are reacted with electrophilic and nucleophilic substances.

It is an object of the present invention to provide a new process for the manufacture of compounds which are substituted in α-position to a carbonyl group. It is another object of the invention to provide a new process for the manufacture of compounds which contain two carbonyl groups in 1,3-position and bear one or two substituents in 2-position. Another object of the invention is the new compounds obtainable by the new process. Further objects and advantages of the invention will be apparent from the following detailed description.

We have found that these objects are achieved by reacting a sulfur ylide which contains the grouping

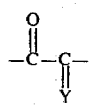

where Y is the radical

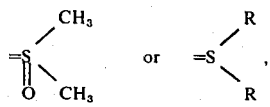

R being alkyl or aryl, with an electrophilic reagent A' and a nucleophilic reagent B' or with a compound AB which formally may be taken to be composed of an electrophilic radical A and a nucleophilic radical B. Electrophilic and nucleophilic reagents, also called electrophiles and nucleophiles, have been described for example in C. K. Ingold, "Structure and Mechanism in Organic Chemistry", 211, Cornell University Press, Ithaka, 1953, and I. D. Roberts and M. Caserio, "Basic Principles of Organic Chemistry", 288, W. A. Benjamin, Inc., New York, 1964.

The process can be represented by the following equation:

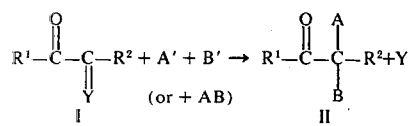

It is assumed that the sulfur ylide first reacts with the electrophile and the resultant intermediate

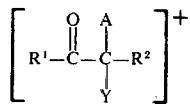

then reacts with the nucleophile to form the desired compound, the sulfur function Y being eliminated.

In the above general formulae, $R^1$ is an aliphatic, araliphatic, aromatic or heterocyclic radical or the group

or $-O-R^5$ where $R^3$ and $R^4$ are hydrogen and $R^3$, $R^4$ and $R^5$ are alkyl, aralkyl, cycloalkyl or aryl radicals; $R^2$ is hydrogen, an alkyl or aralkyl group, the radical

where $R^1$ has the meaning given above, the radical

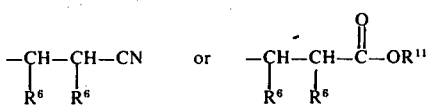

where $R^6$ is hydrogen or the methyl group and $R^{11}$ is an alkyl radical with 1 to 4 carbon atoms;

A is hydrogen, a linear alkyl radical, an aralkyl radical, chlorine, bromine, iodine, a nitrile group, the radical

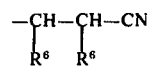

or the radical

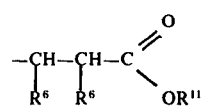

where $R^6$ and $R^{11}$ have the meanings given above;

B is chlorine, bromine, iodine, hydroxy, sulfhydryl, thiocyano (—SCN), cyanato, nitro, azido, the radical —$XR^7$ where X is oxygen, sulfur or the radical —$SO_2$— and $R^7$ is alkyl, aryl, aralkyl and, if X is oxygen or sulfur, may also be the acyl radical

where $R^8$ is linear alkyl, cycloalkyl, aralkyl, phenyl or toluyl, or the group

where $R^3$ and $R^4$ have the meanings given above; and Y is the radical

or the radical

where $R^9$ and $R^{10}$ are linear alkyl groups or phenyl radicals.

The sulfur ylides I which are used as starting materials where Y is the radical

can be prepared for example by the action of isocyanates, ketenes, acid chlorides or acid anhydrides on dimethyl-oxo-sulfonium ylides. The sulfur ylides I which are used as starting materials where Y stands for

can be prepared in an analogous manner or by the action of, for example, tertiary amines or sodium hydride on the corresponding sulfonium salts already containing the carbonyl function. The sulfur ylides I in which $R^2$ is the radical

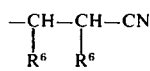

or

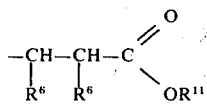

and Y, $R^6$ and $R^{11}$ have the meanings given above, which may also be used as starting materials are obtained by reacting, in a molar ratio of 1:approx. 1, a sulfur ylide of the formula

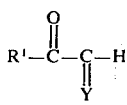

with an α,β-olefinically unsaturated carboxylic nitrile having the formula

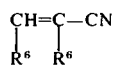

or an α,β-olefinically unsaturated carboxylic ester having the formula

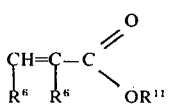

where $R^6$ and $R^{11}$ have the meanings given above. It is not necessary for the purposes of the process to separate the said ylides from the mixtures in which they are obtained in the manufacture. The mixture in which they are obtained may rather be used direct.

In the sulfur ylides which are preferred as starting materials the radical $R^1$ is alkyl having 1 to 12, preferably 1 to 4 carbon atoms, aralkyl having 7 to 10, preferably 7 or 8 carbon atoms, phenyl, o-, m- or p-toluyl or α- or β-naphthyl. The said aromatic substituents may further bear 1 or 2 chlorine or bromine atoms or 1 or 2 alkoxy groups with 1 to 4 carbon atoms. In the preferred ylides I, $R^1$ may further represent a 5- or 6-membered ring having 1 or 2 nitrogen atoms, 1 oxygen or sulfur atom or 1 nitrogen and 1 oxygen or sulfur atom as ring members and if desired bearing an alkyl group with 1 to 4 carbon atoms or a phenyl radical, the radical

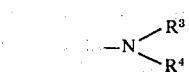

where $R^3$ and $R^4$ are hydrogen, alkyl having 1 to 10, preferably 1 to 4 carbon atoms, cycloalkyl having 5 to 12, preferably 6 to 8 carbon atoms, aralkyl having 7 to 10, preferably 7 or 8 carbon atoms, or phenyl, toluyl or naphthyl. In the preferred ylides I, $R^1$ may finally represent the radical $—OR^5$ where $R^5$ is alkyl having 1 to 12, preferably 1 to 6 carbon atoms, cycloalkyl having 5 to 12, preferably 6 to 8 carbon atoms, aralkyl having 7 to 10, preferably 7 or 8 carbon atoms, or the phenyl, o-, m- or p-chlorophenyl, toluyl or naphthyl radical.

In the sulfur ylides I which are preferred as starting materials the radical $R^2$ is hydrogen, alkyl having 1 to 10, preferably 1 to 4 carbon atoms, aralkyl having 7 to 10, preferably 7 or 8 carbon atoms, the radical

where $R^1$ has the meanings just mentioned, the radical

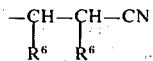

or

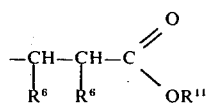

where each of $R^6$ may be hydrogen or methyl and $R^{11}$ is alkyl with 1 to 4 carbon atoms.

In the sulfur ylides I which are preferred as starting materials Y is the radical

or

where $R^9$ and $R^{10}$ are linear alkyl having 1 to 10, preferably 1 to 4 carbon atoms or phenyl radicals.

The following sulfur ylides are examples of suitable starting materials:
benzoyl-dimethyl-oxo-sulfonium methylide,
p-chloro-benzoyl-dimethyl-oxo-sulfonium methylide,
m-toluyl-dimethyl-oxo-sulfonium methylide,
α-naphthoyl-dimethyl-oxo-sulfonium methylide,
4-methoxy-1-naphthoyl-dimethyl-oxo-sulfonium methylide,
phenyl-acetyl-dimethyl-oxo-sulfonium methylide,
β-phenyl-propionyl-dimethyl-oxo-sulfonium methylide,
4-methyl-oxazoloyl-5-dimethyl-oxo-sulfonium methylide,
3-pyridoyl-dimethyl-oxo-sulfonium methylide,
4-pyridoyl-dimethyl-oxo-sulfonium methylide,
3-pyridazoyl-dimethyl-oxo-sulfonium methylide,
ethyl-carboxyl-dimethyl-oxo-sulfonium methylide,
methyl-carboxyl-dimethyl-oxo-sulfonium methylide,
phenyl-carboxyl-dimethyl-oxo-sulfonium methylide,
benzyl-carboxyl-dimethyl-oxo-sulfonium methylide,
β-naphthyl-carboxyl-dimethyl-oxo-sulfonium methylide,
cyclohexyl-carboxyl-dimethyl-oxo-sulfonium methylide or
n-deyl-carboxyl-dimethyl-oxo-sulfonium methylide.
Other sulfur ylides suitable as starting materials include:
N-phenyl-carbamoyl-dimethyl-sulfonium methylide,
N-cyclohexyl-carbamoyl-dimethyl-sulfonium methylide,
N-t-butyl-carbamoyl-dimethyl-sulfonium methylide,
N-isopropyl-carbamoyl-dimethyl-sulfonium methylide,
n-phenyl-ethyl-carbamoyl-dimethyl-sulfonium methylide,
n-benzyl-carbamoyl-dimethyl-sulfonium methylide,
N,N-dimethyl-carbamoyl-dimethyl-sulfonium methylide or
N-p-chloro-phenyl-carbamoyl-dimethyl-sulfonium methylide, and also
bis-benzoyl-dimethyl-sulfonium methylide,
bis-acetyl-dimethyl-sulfonium methylide,
acetyl-benzoyl-dimethyl-sulfonium methylide,
benzoyl-N-cyclohexyl-carbamoyl-dimethyl-sulfonium methylide,
bis-(N-n-octyl-carbamoyl)-dimethyl-sulfonium methylide,
bis-(N-phenyl-carbamoyl)-dimethyl-sulfonium methylide,
bis-(N-cyclohexyl-carbamoyl)-dimethyl-sulfonium methylide,
ethyl-carboxyl-dimethyl-sulfonium methylide,
N-phenyl-carbamoyl-dimethyl-sulfonium methylide,
methyl-(N-propyl-carbamoyl)-dimethyl-sulfonium methylide,
phenyl-ethyl-acetyl-dimethyl-sulfonium methylide,
β-cyanoethyl-N-phenyl-carbamoyl-dimethyl-sulfonium methylide and
β-carbethoxy-ethyl-acetyl-dimethyl-sulfonium methylide.

The following sulfonium ylides are also suitable as starting materials:
S-phenyl-S-methyl-benzoyl-sulfonium methylide,
S,S-di-n-butyl-N-phenyl-carbamoyl-sulfonium methylide,
S,S-diphenyl-acetyl-sulfonium methylide,
S,S-dimethyl-N,N-dimethyl-carbamoyl methylide,
S,S-dimethyl-carboethoxy-sulfonium methylide,
S,S-dimethyl-acetyl-carbobutoxy methylide,
S-phenyl-S-ethyl-N-phenyl-carbamoyl methylide and
S,S-diethyl-bis-(N-cyclohexyl-carbamoyl)-sulfonium methylide.

Preferred electrophiles A' are: elementary chlorine, bromine and iodine, the interhalogen compounds iodine chloride, iodine bromide and bromine chloride, the pseudohalogens cyanogen, cyanogen chloride and cyanogen bromide, acids of boron, phosphorus, sulfur and the halogens which contain protons and have a pK-value of up to 6, e.g. halogen hydracids such as hydrofluoride, hydrochloride, hydrobromide or hydriodide, perchloric acid, sulfuric acid, phosphoric acid or fluoboric acid, sulfonic acids such as benzenesulfonic acid or toluenesulfonic acids, methanesulfonic acid, carboxylic acids, e.g. lower fatty acids, such as formic acid, acetic acid, propionic acid or butyric acid, halogen fatty acids such as mono-, di- and trifluoroacetic acid, mono-, di- and trichloroacetic acid and mono-, di- and tribromoacetic acid, unsubstituted benzoic acid or benzoic acid bearing 1 to 3 chlorine atoms or a nitro group as substituents, and oxalic acid. Other preferred electrophiles A' are alkylating and aralkylating agents such as alkyl and aralkyl chlorides, alkyl and aralkyl bromides, alkyl and aralkyl iodides and alkyl sulfates, and also benzene alkyl sulfonates and toluene alkyl sulfonates, the said alkylating agents having linear alkyl groups with 1 to 10 carbon atoms and the said aralkylating agents having aralkyl radicals with 7 to 12, preferably 7 to 10 carbon atoms. Examples of suitable alkylating and aralkylating agents are methyl chloride, ethyl bromide, butyl iodide, decyl iodide, dimethyl sulfate, diethyl sulfate, butyl benzene sulfonate, octyl p-toluene sulfonate, benzyl chloride or γ-phenylpropyl bromide. Other preferred electrophiles are α,β-olefinically unsaturated carboxylic nitriles and esters having the formula

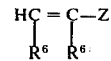

where $R^6$ is hydrogen or the methyl radical, Z is the nitrile group or the group

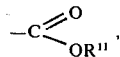

$R^{11}$ being alkyl with 1 to 4 carbon atoms. Suitable starting materials of this type include for example acrylonitrile, methacrylonitrile, crotononitrile, ethyl acrylate, tert.-butyl methacrylate and methyl crotonate.

Examples of preferred nucleophiles B' are halogen ions such as chloride, bromide or iodide ions, pseudohalogen ions such as cyanide, thiocyanate (—SCN), cyanate or azide ions and nitrite hydroxyl or sulfhydryl ions. These nucleophiles are preferably introduced into the reaction vessel in the form of alkali metal, alkaline earth metal or ammonium compounds. Other preferred nucleophiles may be represented by the formula $$H - X - R^7$$

where X is oxygen, sulfur or the —SO$_2$ radical and R$^7$ is alkyl having 1 to 12, preferably 1 to 4 carbon atoms, aryl, preferably phenyl, or aralkyl having 7 to 12, preferably 7 to 10 carbon atoms. If X is oxygen or sulfur, then R$^7$ may also be an acyl radical

where R$^8$ is linear alkyl having 1 to 10, preferably 1 to 4 carbon atoms, cycloalkyl having 5 to 8 carbon atoms, aralkyl having 7 to 12, preferably 7 to 10 carbon atoms or the phenyl or toluyl radical.

Instead of the nucleophiles of the formula $$H - X - R^7$$

the corresponding alkali metal, alkaline earth metal or ammonium compounds may be used. Furthermore, hydrogen sulfide, ammonia or amines of the formula

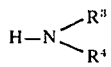

where R$^3$ is hydrogen, phenyl or naphthyl and R$^3$ and R$^4$ are alkyl having 1 to 10, preferably 1 to 4 carbon atoms, cycloalkyl having 5 to 12, preferably 6 to 8 carbon atoms, or aralkyl having 7 to 10, preferably 7 or 8 carbon atoms, are suitable nucleophiles. Thus for example the following nucleophiles may be used: lithium chloride, sodium bromide, potassium iodide, calcium hydroxide, calcium cyanate, potassium cyanide, magnesium thiocyanate, sodium azide, barium nitrite, ammonium chloride, tetramethylammonium iodide, potassium sulfide, sodium hydrogen sulfide, methanol, butanol, octanol, benzyl alcohol, phenol, thiophenol, ethyl mercaptan, benzyl sulfide, benzenesulfinic acid, amylsulfinic acid, thioacetic acid, formic acid, propionic acid, benzoic acid, cyclohexanecarboxylic acids, phenylacetic acid, p-toluic acid, sodium acetate, lithium thio phenolate, tetramethylammonium benzoate, sodium butylate, ammonium formate, ammonia, dimethylamine, diethylamine, aniline, methylaniline, benzylamine, cyclopentylamine, cyclooctylamine and p-toluidine.

It is also possible to use compounds of the type AB which are capable of reacting both as electrophiles and as nucleophiles. Such substances are the hydracids of chlorine, bromine and iodine, elementary chlorine, bromine and iodine, the said alkyl halides, interhalogen compounds and pseudohalogens. It will be understood that some compounds may react both as electrophiles and as compounds of the type AB. For example, hydrogen chloride is capable of acting as a compound of the AB type, its proton being present in the reaction product as hydrogen atom A and its chloride ion as chlorine atom B. On the other hand, hydrogen chloride may act merely as an electrophile, namely when a nucleophile is present which reacts more readily or more quickly with the ylide I than the chloride ion of hydrogen chloride. This is the case for example when reacting an ylide I with hydrogen chloride and aniline (cf. Example 4). Other examples are elementary halogens which either supply the substituents A and B in the reaction products or merely participate with a halogen cation as electrophile which yields a halogen atom A in the reaction product, whereas substituent B is supplied by a different nucleophile.

The process according to this invention is preferably carried out in the presence of solvents which are inert under the reaction conditions. Suitable solvents include hydrocarbons such as benzene, toluene, the xylenes, cyclohexane or heptane, chlorinated hydrocarbons such as carbon tetrachloride, dichloroethylene, chloroform or chlorobenzene, ethers such as tetrahydrofuran, dioxane, dibutyl ether or anisol, N,N-disubstituted carboxylic amides such as N,N-dimethylformamide, N,N-diethylformamide, N-methylpyrrolidone or N-butylpyrrolidone, water, dimethyl sulfoxide, tetramethylene sulfone of acetonitrile. If reactants are used which are liquid under the reaction conditions, these may act as solvents. For example the said alcohols may be used both as solvents and as reactants.

To carry out the process according to the present invention it is possible to first add the electrophile and then the nucleophile to a solution or suspension of the sulfur ylide. It is also possible however to add the ylide to the electrophile and then to introduce the nucleophile, either as such or in solution or to mix the ylide with a compound of the type AB. Another possibility is to produce the ylide in the presence of the other reactants, so that the ylide formed reacts in situ. The process may be carried out within a broad range of temperatures, as a rule between 0° and 150°C, preferably between 25° and 120°C. It is expedient to stir the reaction mixture. If relatively volatile substances are to be reacted at temperatures above their boiling points it is expedient to use superatmospheric pressure, for example pressures between 1 and 50 atmospheres. The process may be carried out either continuously or batchwise. Isolation of the compounds obtainable by the process may be effected, for example, by fractionation, by extraction with a suitable solvent or, if the reactants crystallize out from the reaction mixture or are separated by the addition of a precipitant, by filtration or centrifuging.

By reacting a sulfur ylide I where the radical R$^2$ is

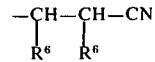

or

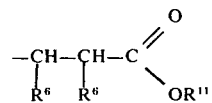

with an α,β-olefinically unsaturated carboxylic nitrile or carboxylic ester having the formula

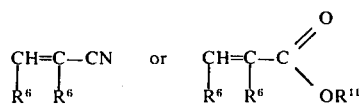

where $R^6$ and $R^{11}$ have the meanings given above at temperatures which are preferably between 0° and 70°C in the presence of an alcohol having the formula $R^{11}$—OH where $R^{11}$ has the meanings given above, a compound having the general formula

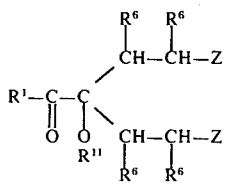

is obtained where $R^1$, $R^6$ and $R^{11}$ have the meanings given above and Z is the nitrile group or the group

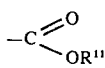

The compounds obtainable by the process according to the present invention are valuable starting materials for the manufacture of paper, textile and leather auxiliaries. They may also be used for the manufacture of plant protection agents. Those compounds which are covered by the formula

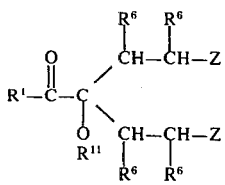

where the radicals $R^1$, $R^6$, $R^{11}$ and Z have the preferred meanings mentioned above are new. By alkaline or acid hydrolysis of the nitrile or carboxylic ester groups referred to as Z at temperatures between for example 20° and 100°C dicarboxylic acids are obtained, and tricarboxylic acids are obtained if $R^1$ is the radical

or

The dicarboxylic acids may be condensed analogously to the reaction of adipic acid to polyamides. By reaction with glycols at temperatures of about 200° to 250°C valuable linear polyesters are obtained. The tricarboxylic acids are valuable starting materials for the manufacture of alkyd resins (branched polyesters).

The invention is further illustrated by the following Examples. The parts specified are by weight.

EXAMPLE 1

3.30 parts of dimethyl-oxo-sulfurylene malonic dianilide is dissolved in 40 parts of chloroform and slowly mixed with a solution of 1.60 parts of bromine in 40 parts of chloroform. After 20 minutes the colorless solution is evaporated to dryness and the residue is dissolved in and reprecipitated from hexane. 3.36 parts of $\alpha,\alpha$-dibromomalonic dianilide of the melting point 148° to 150°C, i.e. 80% of the theory, based on dimethyl-oxo-sulfurylene malonic dianilide used, is obtained.

EXAMPLE 2

3.08 parts of dimethyl-oxo-sulfurylene malonic acid-N,N'-cyclohexyl diamide and 3.2 parts of bromine are heated under reflux in chloroform. After 10 minutes the solution is evaporated to dryness and the residue is dissovled in and reprecipitated from cyclohexane. 3.80 parts (90% of the theory) of $\alpha,\alpha$-dibromo-N,N'-cyclohexylmalonic diamide of the melting point 138°C is obtained. The yield is 90% of the theory, based on dimethyl-oxo-sulfurylene malonic acid-N,N'-cyclohexyl diamide used.

EXAMPLE 3

3.30 parts of dimethyl-oxo-sulfurylene malonic dianilide and 60 parts of concentrated hydrochloric acid are heated under reflux for 10 minutes. The precipitate ist filtered off by suction and dissolved in and reprecipitated from cyclohexane. 2.83 parts of $\alpha$-chloromalonic dianilide of the melting point 173° to 174°C is obtained. This is a yield of 90% of the theory, based on dimethyl-oxo-sulfurylene malonic dianilide used.

EXAMPLE 4

1.06 parts of dimethyl-oxo-sulfurylene acetanilide, 20 parts of aniline and 15 parts of aniline hydrochloride are heated at the boil for 3 minutes in an atmosphere of nitrogen. The excess aniline is distilled off at 10 mm Hg and the residue recrystallized from dilute hydrochloric acid. 8.5 parts of $\alpha$-anilino-acetanilide hydrochloride of the melting point 216°C is obtained. The yield is 65% of the theory, based on dimethyl-oxo-sulfurylene acetanilide used.

EXAMPLE 5

4.00 parts of dimethyl-oxo-sulfurylene acetanilide, 2.10 parts of thiophenol and 10 parts of dimethylformamide are mixed with 0.1 part of p-toluenesulfonic acid to give a clear solution. The solution is allowed to stand for 10 hours at 25°C and then stirred into ice water and filtered off by suction. The residue is washed and dried. 3.73 parts of phenylthio acetanilide (i.e. 81% of the theory) of the melting point 79°C is obtained. After dissolution in and reprecipitation from cyclohexane the melting point is 81°C.

EXAMPLE 6

4.22 parts of dimethyl-oxo-sulfurylene acetanilide, 40 parts of freshly distilled acrylonitrile and 40 parts of methanol are heated under reflux for 45 minutes. The readily volatile constituents are distilled off. The residue is taken up in 200 parts of benzene, washed with 300 parts of water in three portions, and the benzene extract is concentrated and dissolved in and reprecipitated from cyclohexane and ethyl acetate. 2.02 parts of crystalline $\gamma$-methoxy-$\gamma$-carbanilido-$\alpha,\omega$-dicyclopentane of the melting point 82°C is obtained. The yield is 40% of the theory, based on dimethyl-oxo-sulfurylene acetanilide.

Analysis: $C_{15}H_{17}N_3O_2$ (271.3) Calculated: C 66.5%; H 6.5%; N 15.5%; O 11.8%; Found: C 66.5%; H 6.3%; N 15.2%; O 12.3%

EXAMPLE 7

4.22 parts of dimethyl-oxo-sulfurylene acetanilide, 5 parts of methyl iodide and 500 parts of methanol are kept at 20°C for 100 hours. The methanol is then distilled off at subatmospheric pressure (20°C/10 mm Hg) and the residue is recrystallized from methanol diluted with water. 2.15 parts of α-iodopropionic anilide of the boiling point 131°C is obtained. The yield is 39% of the theory, based on dimethyl-oxo-sulfurylene acetanilide used.

EXAMPLE 8

44 parts of trimethyl-oxo-sulfonium iodide and 5.34 parts of 90% sodium hydride are dissolved in 400 parts of dimethyl sulfoxide. A solution of dimethyl-oxo-sulfonium methylide is thus obtained to which 29.2 parts of methyl benzoate is quickly added. The mixture ist stirred for 80 hours at 25°C. The reaction mixture, which is then neutral, is freed from sodium benzoate by filtration. 14.5 parts of trimethyl-oxo-sulfonium iodide is precipitated from the filtrate with acetone and ethyl acetate and filtered off by suction. The solvent are removed from the filtrate by distillation under reduced pressure and 5.05 of α-benzoxy-ethyl-phenyl ketone of the melting point 106°C is obtained by extraction of the residue with ethanol. The yield is 40% of the theory, based on trimethyl-oxo-sulfonium iodide.

EXAMPLE 9

242 parts of δ,δ-diphenyl-acetyl-sulfonium methylide, 142 parts of benzenesulfinic acid, 10 parts of p-toluenesulfonic acid and 1000 parts of methanol are stirred for 20 hours at 50°C. The solution is concentrated and cooled and the crude reaction product is filtered off by suction. By dissolution in and reprecipitation from ethanol 140 parts of phenylsulfonyl acetone of the melting point 57° to 58°C is obtained.

EXAMPLE 10

118 parts of δ,δ-dimethyl-acetyl-sulfonium methylide, 192 parts of α-naphthylsulfinic acid, 10 parts of oxalic and 2000 parts of tetrahydrofuran are stirred for 100 hours under reflux. The solvent is then removed and the residue consisting of 270 parts is dissolved in and reprecipitated from ethyl acetate. Acetonyl-α-naphthyl sulfone of the melting point 65°C is obtained.

In an analogous manner benzyl phenacyl sulfone of the melting point 89°C (sample recrystallized from ethanol) is obtained in a 60% yield from δ,δ-dimethyl-benzoyl-oxo-sulfonium methylide and benzylsulfinic acid in the presence of fluoboric acid and using benzene as solvent.

By using δ,δ-diphenyl-carboethoxy-sulfonium methylide, and equivalent amounts of hydrogen chloride and benzenesulfinic acid, the ethyl ester of phenyl sulfonyl acetate of the melting point 45°C is obtained (recrystallized from benzene).

Ethyl sulfonyl acetamide, melting point 99°C (recrystallized from alkanol), is obtained from δ-ethyl-δ-phenyl-carbamoyl-sulfonium methylide, ethylsulfinic acid and phosphoric acid when using tetramethylene sulfone as solvent.

EXAMPLE 11

148 parts of δ,δ-dimethyl-carboethoxy-sulfonium methylide, 154 parts of diethyl sulfate and 1000 parts of acetonitrile are stirred for 2 hours. 164 parts of sodium benzene sulfinate is then added and the whole heated for 10 hours at 80°C. The solvent is removed and the residue recrystallized from petroleum ether. 203 parts of the ethyl ester of α-phenyl sulfonyl butyric acid of the melting point 63° to 64°C is obtained.

EXAMPLE 12

119 parts of δ,δ-diethyl-N-phenyl-carbamoyl-sulfonium methylide is heated to 60°C in 1000 parts of dimethylsulfoxide together with 84 parts of trifluoroacetic acid and hydrogen sulfide at a pressure of 5 atmospheres gauge. The reaction mixture is poured on to ice and the crude product, which is slightly smeary, is filtered off with suction and recrystallized from methanol. 60 parts of thioglycolic acid anilide of the melting point 111°C is obtained.

The N-methylthioglycolic acid anilide of the melting point 143°C is obtained in an analogous manner.

EXAMPLE 13

By using n-propyl mercaptan instead of hydrogen sulfide and otherwise proceeding as described in Example 12, 72 parts of n-propylmercaptoacetic anilide of the melting point 57°C is obtained. The reaction mixture is poured on to ice and the product preferably extracted with ether.

EXAMPLE 14

180 parts of δ,δ-dimethyl-benzoyl-sulfonium methylide, 10 parts of p-toluenesulfonic acid and 124 parts of benzyl mercaptan are stirred for 100 hours in 1500 parts of chlorobenzene at 20°C. The solvent ist distilled off and the residue recrystallized from ethanol. The α-benzylmercaptoacetophenone thus obtained melts at 87°C.

EXAMPLE 15

A suspension of 209 parts of δ,δ-dimethyl-N-methyl-N-phenyl-carbamoyl-sulfonium methylide in 500 parts of water which contains 46 parts of formic acid is stirred with 100 parts of ammonium thiocyanate for 36 hours. By extracting with methylene chloride, drying the solution, removing the solvent and recrystallizing from ethanol 170 parts of α-thiocyanoacetic acid-N-methyl anilide is obtained which melts at 79°C.

α-thiocyanoacetic acid-p-toluidide melting at 126°C is obtained in an analogous manner.

EXAMPLE 16

58 parts of acetic acid and then 70 parts of sodium azide and 10 parts of lithium chloride are added while stirring to a suspension of 223 parts of δ,δ-dethyl-N-phenyl-carbamoyl-sulfonium methylide in 2000 parts of tetrahydrofuran. The whole is stirred for 50 hours under reflux and then diluted with water. The δ-azidoazetanilide is extracted with benzene and the extract is concentrated and dissolved in and reprecipitated from benzene. 103 parts of α-azidoacetanilide melting at 83°C is obtained.

EXAMPLE 17

118 parts of δ,δ-dimethyl-acetyl-sulfonium methylide and 200 parts of formic acid are heated for 10 hours under reflux. The liquid reaction mixture is then fractionally distilled. 60 parts of acetonyl formate melting at 169°C is obtained.

EXAMPLE 18

220 parts of δ,δ-dimethyl-N-phenyl-carbamoyl-oxo-sulfonium methylide and 84 parts of trifluoroacetic acid are stirred at 60°C with 80 parts of sodium nitrite in 500 parts of dimethyl sulfoxide. After 12 hours the reaction mixture is stirred into ice water and the precipitate is filtered off by suction. 139 parts of nitroacetanilide, melting point 139°C, is obtained.

EXAMPLE 19

242 parts of δ,δ-diphenyl-acetyl-sulfonium methylide and 172 parts of methyl benzene sulfonate are mixed intensely for one hour with 200 parts of acetonitrile. Then 65 parts of potassium cyanide is added and the reaction mixture is heated to 80°C with intense agitation. After 10 hours the mixture is filtered with suction, washed with ether and the filtrate distilled. The fraction boiling at 145° to 148°C is 2-cyanobutanone-3.

EXAMPLE 20

148 parts of δ,δ-dimethyl-carboethoxy-sulfonium methylide and 106 parts of cyanogen bromide are stirred for 8 hours in 2000 parts of ether. The ether is distilled off and 150 parts of the ethyl ester of δ-bromocyanoacetic acid is obtained.

EXAMPLE 21

196 parts of δ,δ-dimethyl-dicarboethoxy-sulfonium methylide, 172 parts of p-toluenesulfonic acid and 213 parts of barium nitrite are stirred at 25°C for 100 hours in 1800 parts of methanol. The mixture is concentrated, the residue washed with ether and the dimethyl nitro malonate is extracted and subsequently fractionated at 10 mm Hg at 122°C.

EXAMPLE 22

118 parts of δ,δ-dimethyl-acetyl-oxo-sulfonium methylide is heated under reflux together with 800 parts of methacrylonitrile and 800 parts of ethanol until evolution of dimethyl sulfide ceases. The low-boiling constituents are distilled off under subatmospheric pressure and an oily residue is obtained which by infrared spectroscopy can be shown to contain a keto group, a nitrile group and an ether goup. Pure 2,6-dicyano-4-ethoxy-4-acetylheptane is obtained chromatographically on aluminum oxide as a colorless oil.

Analysis: $C_{13}H_{20}N_2O_2$ (236): Calculated: C 65.2%; H 8.5%; N 11.9%; O 13.6%; Found: C 64.8%; H 8.2%; N 12.4%; O 14.0%

2,4-dimethyl-3-benzoyl-33-butoxypentane-1,5-dicarboxylic acid-di-n-butyl ester is obtained as a pale yellow oil in an analogous manner from δ,δ-dimethyl-benzoyl-sulfonium methylide, n-butyl crotonate and n-butanol.

Analysis: $C_{28}H_{44}O_6$ (476) Calculated: C 70.7%; H 9.3%; O 20.2%; Found: C 70.5%; H 9.5%; O 20.8%

EXAMPLE 23

284 parts of δ,δ-dimethyl-dibenzoyl-sulfonium methylide is heated to 80°C while adding first an an equivalent amount of dimethyl sulfate and then an equivalent amount of sodium phenolate in 1000 parts of methylene sulfone. The solvent is removed at subatmospheric pressure. Phenoxydibenzoylethane is obtained as a viscous pale yellow oil.

Analysis: $C_{22}H_{18}O_3$ (330): Calculated: C 80.1%; H 5.5%; O 16.6%; Found: C 79.7%; H 5.8%; O 17.0%.

The following compounds are also obtained by the process according to the present invention:
α-iododibenzoylmethane, m. p. 107°C.
Thioglycolic acid-α-naphthylamide, m.p. 128°C.
Benzylmercapt acetone, b. p. 155°C.
Methylmercapto acetanilide, m. p. 74°C.
Nitro acetone, m. p. 49°C.
Ethyl cyano acetate, b. p. 98°C (18 mm).
n-butylmercapto propionamide, m. p. 65°C.
Thiocyano acetanilido, m. p. 86°C.
Methyl n-butyloxy acetate, b. p. 180°C.
Ethyl α-[4-pyridoyl]-α-iodo propionate, m. p. 63°C.
Lactic anilide, m. p. 58°C.

We claim:

1. A process for the manufacture of carbonyl compounds substituted in α-position and having the formula:

where $R^1$ is an alkyl radical having 1 to 12 carbon atoms, an aralkyl radical having 7 to 8 carbon atoms, a phenyl, o-toluyl, m-toluyl, p-toluyl, α-naphthyl or β-naphthyl radical which may bear 1 chlorine atom or 1 methoxy group as substituents, the group

where $R^3$ and $R^4$ are selected from the group consisting of hydrogen, alkyl of 1 to 10 carbon atoms, cyclohexyl, benzyl, phenyl, toluyl, p-chlorophenyl, and naphthyl or the radical $-OR^5$ where $R^5$ is alkyl of 1 to 4 carbon atoms, $R^2$ is hydrogen, the radical

where $R^1$ has the meaning given above, the radical

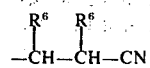

or the radical

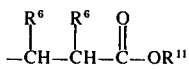

where $R^6$ is hydrogen or methyl and $R^{11}$ is alkyl of 1 to 4 carbon atoms, A is hydrogen, linear alkyl of 1 to 10 carbon atoms, chlorine, bromine, iodine, the radical

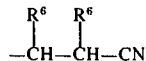

or the radical

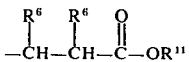

where $R^6$ and $R^{11}$ have the meanings given above, B is chlorine, bromine, iodine, hydroxy, sulfhydryl, thiocyano, cyanato, nitro, azido, the radical $-XR^7$ where X is oxygen, sulfur or the radical $-SO_2-$ and $R^7$ is alkyl having 1 to 4 carbon atoms, phenyl, naphthyl, benzyl, or if X is oxygen or sulfur, the acyl radical

where $R^8$ is hydrogen, phenyl or toluyl, or the group

where $R^3$ and $R^4$ have the meanings given above, which comprises reacting a sulfur ylide having the formula:

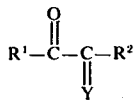

where $R^1$ and $R^2$ have the meanings given above and Y is the radical

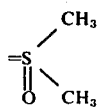

or the radical

where $R^9$ and $R^{10}$ are linear alkyl groups having 1 to 4 carbon atoms or phenyl radicals, with a solution which contains both an electrophilic agent A' that is converted into said radical A and a nucleophilic agent B' that is converted into said radical B or contains a compound of the type AB capable of reacting both as A' and as B', or first with a solution which contains said electrophilic agent A' and then with a solution which contains said nucleophilic agent B', at temperatures between 0° and 150°C, A' being chlorine, bromine, iodine, cyanogen, cyanogen chloride, cyanogen bromide, an alkyl bromide, iodide, sulfate or sulfonate of 1 to 10 carbon atoms, an aralkyl bromide, iodide, sulfate or sulfonate of from 6 to 15 carbon atoms, or an α,β-olefinically unsaturated carboxylic nitrile or ester having the formula

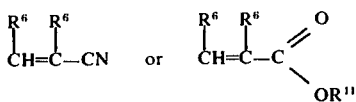

where $R^6$ and $R^{11}$ have the meanings given above, the solution of said electrophilic agent A' containing an amount of protons at least equivalent to the amount of nitrile or ester to be reacted if A' is one of the said carboxylic acid derivatives, and B' in said solution being a chloride, bromide, iodide, hydroxide, alkanolate having 1 to 4 carbon atoms, phenolate, sulfide, phenyl sulfide, ethyl sulfinate, naphthylsulfinate, phenyl sulfinate, benzyl sulfinate, cyanide, thiocyanate, azide or nitrite of an alkali metal, an alkaline earth metal or ammonium or being an amine having the formula

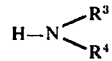

where $R^3$ and $R^4$ have the meanings given above, water, hydrogen sulfide or a compound having the formula H — X — $R^7$ where $R^7$ and X have the meanings given above.

* * * * *